(12) United States Patent
Hawkes et al.

(10) Patent No.: US 9,364,403 B2
(45) Date of Patent: Jun. 14, 2016

(54) HAIR TREATMENT METHODS

(71) Applicant: Perachem Limited, Leeds (GB)

(72) Inventors: Jamie Anthony Hawkes, Leeds (GB); David Malcolm Lewis, Otley (GB); John Mama, Leeds (GB)

(73) Assignee: Perachem Limited, Yeadon, Leeds (GB)

( * ) Notice: Subject to any disclaimer, the term of this patent is extended or adjusted under 35 U.S.C. 154(b) by 0 days.

(21) Appl. No.: 14/389,950

(22) PCT Filed: Mar. 22, 2013

(86) PCT No.: PCT/GB2013/050757
§ 371 (c)(1),
(2) Date: Oct. 1, 2014

(87) PCT Pub. No.: WO2013/150269
PCT Pub. Date: Oct. 10, 2013

(65) Prior Publication Data
US 2015/0068548 A1  Mar. 12, 2015

(30) Foreign Application Priority Data

Apr. 2, 2012 (GB) .................................. 1205911.9
Jun. 18, 2012 (EP) .................................. 12275094

(51) Int. Cl.
*A61Q 5/10* (2006.01)
*A61K 8/46* (2006.01)
(Continued)

(52) U.S. Cl.
CPC . *A61K 8/466* (2013.01); *A61K 8/19* (2013.01); *A61K 8/23* (2013.01); *A61K 8/42* (2013.01); *A61K 8/447* (2013.01); *A61K 8/46* (2013.01); *A61Q 5/10* (2013.01); *A61Q 5/12* (2013.01); *A61K 2800/30* (2013.01); *A61K 2800/4324* (2013.01); *A61K 2800/884* (2013.01)

(58) Field of Classification Search
CPC ........... A61Q 5/10; A61K 8/466; A61K 8/19; A61K 8/23; A61K 8/46; A61K 8/447; A61K 2800/4324
USPC ............................................................. 8/405
See application file for complete search history.

(56) References Cited

U.S. PATENT DOCUMENTS

| | | | |
|---|---|---|---|
| 3,396,736 A | | 8/1968 | Shansky |
| 3,399,682 A | * | 9/1968 | Isaji ........................ A61K 8/46 |
| | | | 132/204 |

(Continued)

FOREIGN PATENT DOCUMENTS

| | | |
|---|---|---|
| DE | 10055947 A1 | 5/2002 |
| EP | 1366755 A1 | 12/2003 |

(Continued)

OTHER PUBLICATIONS

International Search Report, PCT/GB2013/050757, entitled "Hair Treatment Methods," mailed Dec. 6, 2013.

(Continued)

*Primary Examiner* — Eisa Elhilo
(74) *Attorney, Agent, or Firm* — HoustonHogle, LLP

(57) ABSTRACT

A coloring composition comprising: (i) at least 0.0001 wt % of a water-soluble dye compound containing one or more sulfonate and/or carboxylate groups; (ii) at least 0.1 wt % urea; (iii) from 0.1 to 2.5 wt % of a thiol; (iv) less than 0.5 wt % ammonia; and (v) less than 0.5 wt % sulfite ions.

9 Claims, 3 Drawing Sheets

Example 1     Example 2

(51) Int. Cl.
| | |
|---|---|
| *A61K 8/42* | (2006.01) |
| *A61K 8/44* | (2006.01) |
| *A61K 8/19* | (2006.01) |
| *A61K 8/23* | (2006.01) |
| *A61Q 5/12* | (2006.01) |

(56) References Cited

U.S. PATENT DOCUMENTS

| | | | |
|---|---|---|---|
| 3,892,845 | A | 7/1975 | Cunningham et al. |
| 5,376,146 | A | 12/1994 | Casperson et al. |
| 6,379,657 | B1 | 4/2002 | Lorenz et al. |
| 6,398,822 | B1 | 6/2002 | Brock et al. |
| 7,413,579 | B2 | 8/2008 | Seiler et al. |
| 7,972,388 | B2 | 7/2011 | Hamilton et al. |
| 2004/0244126 | A1 | 12/2004 | Vena et al. |
| 2012/0141398 | A1 | 6/2012 | Chuang |
| 2015/0047131 | A1 | 2/2015 | Hawkes et al. |

FOREIGN PATENT DOCUMENTS

| | | | |
|---|---|---|---|
| EP | 1 313 83 B1 | | 7/2005 |
| EP | 1 313 830 B1 | | 7/2005 |
| EP | 2382962 A1 | | 11/2011 |
| GB | 951 021 | | 3/1964 |
| GB | 1 077 758 | | 8/1967 |
| GB | 1077758 | * | 8/1967 |
| WO | WO 03/074016 A1 | | 9/2003 |
| WO | 2007/146672 A2 | | 12/2007 |
| WO | 2009/009653 A2 | | 1/2009 |
| WO | WO 2009/112858 A2 | | 9/2009 |
| WO | WO 2010/032030 A2 | | 3/2010 |
| WO | WO 2010/032034 A2 | | 3/2010 |
| WO | WO 2010/097339 A2 | | 9/2010 |
| WO | WO 2012/113724 A2 | | 8/2012 |

OTHER PUBLICATIONS

Written Opinion, PCT/GB2013/050757, entitled "Hair Treatment Methods," mailed Dec. 6, 2013.
Search Report, GB 1305301.2, dated Aug. 6, 2013.
Search Report, GB 1316255.7, dated Oct. 14, 2013.
Search Report, GB 1305313.7, dated May 14, 2013.
International Preliminary Report on Patentability (IPRP) for PCT/GB2013/050757, entitled "Hair Treatment Methods," issued Oct. 16, 2014.
Database GNPD (online, http://www.gnpd.com) Mintel: "Permanent Hair Colourant Cream," Access. No. 1380589 Sep. 2010.
Zhou et al. "Protection of oxidative hair color fading from shampoo washing by hydrophobically modified cationic polymers," J. Cosmet. Sci. 60, 217-238 (Mar./Apr. 2009).
International Search Report, from International Application No. PCT/GB2013/050756, filed on Mar. 22, 2013.
Written Opinion, from International Application No. PCT/GB2013/050756, filed on Mar. 22, 2013.
International Preliminary Report on Patentability, from International Application No. PCT/GB2013/050756, filed on Mar. 22, 2013.
Office Action dated Jul. 27, 2015, from U.S. Appl. No. 14/389,925.
Liu, Cheng et al., "Surfactant Property Theory and Application," Beijing University of Technology Press, Jun. 30, 2003, pp. 727-728.
Translation (three pages) of the Chinese-language reference cited by the Chinese Intellectual Property Office in an Office Action mailed from the CIPO on Feb. 23, 2016 in a corresponding application.
Chinese Office Action, Application No. 20130023687.4, mailed Feb. 23, 2016. Thirteen pages.

* cited by examiner

| Example 1 | Example 2 |

| Example 4 | Example 5 |

HAIR TREATMENT METHODS

This application is the U.S. National Stage of International Application No. PCT/GB2013/050757, filed Mar. 22, 2013, which designates the U.S., published in English, and claims priority under 35 U.S.C. §§119 or 365(c) to Great Britain Application No. 1205911.9 filed Apr. 2, 2012 and European Application No. 12275094.6 filed Jun. 18, 2012.

The present invention relates to methods for colouring materials, in particular colouring keratinous fibre materials, for example hair.

The colouring of human hair is a long-established practice in many cultures. There are many challenges for those working in the field of hair colouration. It is desirable to provide dyes and dyeing methods by which hair can be predictably coloured to consistently provide the desired shade. Hair colouring methods should be efficient in order to allow short contact times which provide wash durable and light durable colour and any damage to the hair should be kept to a minimum.

It is desirable to offer a user a wide range of colours for use in hair colouration. It would also be highly desirable to provide a hair colour which is durable to normal washing of the hair but which can be easily removed from the hair if desired. Current methods of removing artificial colour from the hair involve oxidatively bleaching the dyed hair which causes damage to the hair and does not usually return the hair to its original pre-dyed colour.

Permanent hair colouring compositions of the prior art have typically included colourless dye precursor compounds which react in situ via an oxidative coupling mechanism to form the coloured species. One problem with such compositions is that the colour may continue to develop for several hours or days after application and thus it may be difficult to predictably achieve the desired colour. It is also known to use reactive dye compounds in permanent hair colouring compositions.

The colour chemist is also aware of many other dye classes which offer a wide variety of different colours. However many previous attempts to colour hair using these different classes of dye have been unsuccessful due to poor wash fastness and poor build up of the colour produced. It is known to use some pre-formed chromophores available in the textile industry as semi-permanent hair dyes. However such compounds have not previously been successfully used to permanently dye human hair.

It is an aim of the present invention to provide alternative hair dye compositions and methods, in particular for use in permanent dyeing of human hair.

According to a first aspect of the present invention there is provided a colouring composition comprising:
  (i) at least 0.0001 wt % of a water-soluble dye compound containing one or more sulfonate and/or carboxylate groups;
  (ii) at least 0.1 wt % urea;
  (iii) from 0.1 to 2.5 wt % of a thiol;
  (iv) less than 0.5 wt % ammonia; and
  (v) less than 0.5 wt % sulfite ions.

According to a second aspect of the present invention there is provided a method of colouring a material, the method comprising contacting the material with a colouring composition of the first aspect.

Preferred features of the first and second aspects will now be further defined.

The composition of the present invention comprises at least 0.0001 wt % of a water soluble dye compound containing sulfonate and/or carboxylate groups.

By this we mean that the dye compound includes at least one carboxylate group or at least one sulfonate group.

The dye compounds used in the composition of the present invention may include more than one carboxylate group and/or more than one sulfonate groups.

By carboxylate group we mean to refer to the residue of a carboxylic acid, $-CO_2^-$. By sulfonate group we mean to refer to the residue of a sulfonic acid $-SO_3^-$.

BRIEF DESCRIPTION OF THE DRAWINGS

FIG. 3A shows un-dyed bleached dark brown hair; FIG. 3B shows hair dyed using the formulation of Example 7, comparative; and FIG. 3C shows hair dyed using the formulation of Example 1.

Figure 1:
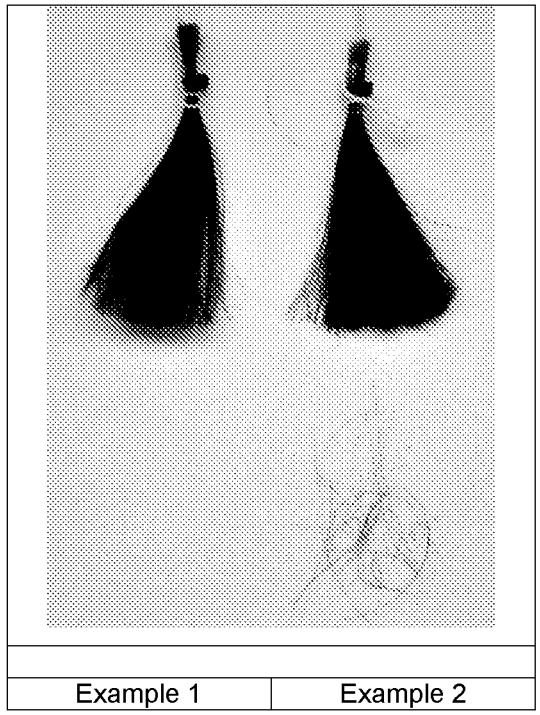
FIG. 1 is a photograph showing hair tresses treated according to Example 1 (left side of the photograph) and Example 2 (right side of the photograph). Hair tresses treated with the composition of Example 1 showed no breakage of the hair while hair treated with the composition of Example 2 showed significant breakage.

The carboxylate and/or sulfonate groups may be present as the free acid i.e. $-COOH$ or $-SO_3H$. Preferably they are present as the salt of the acid i.e., $-COO^-M^+$ or $-SO_3^-M^+$ where $M^+$ is a cation. Suitable cations include ammonium or substituted ammonium cations, and alkali metal and alkaline earth metal cations. Preferred are alkali metal cations, for example sodium and potassium cations. Most preferably the carboxylate and/or sulfonate groups are present as their sodium salts.

The dye compounds of the present invention also include a chromophore. Preferably the dye compound includes a chromophore that is active in the visible region of the electromagnetic spectrum. However dye molecules including a chromophore that is active in the ultraviolet or infrared region of the electromagnetic spectrum are also within the scope of the invention.

The dye compounds used in the compositions of the present invention may include dye compounds generally known to those skilled in the art as acid dyes, including the classes of acid milling dyes and acid levelling dyes.

Acid dyes are typically water soluble anionic dyes that contain one or more sulphonic acid groups, usually as the sodium salt, carboxylic acid groups or hydroxyl groups (less common). The structure on which the dyes are based depends on the colour. Acid dyes can be based on a number of chromophores, which tend to dictate the colour of the dye. For example, blue acid dyes are often based on an anthraquinone moiety, or triphenylmethane, although some may be azo based, formazan or phthalocyanine based. Red, orange and yellow acid dyes tend to be based upon azo moieties.

Compounds based on stillbene or coumarin including carboxylate and/or sulfonate residues may be useful in compositions for providing special effects. Such compounds are known to be fluorescent.

Preferably the dye compounds used in the compositions of the present invention do not include any transition metals.

Preferably the dye compounds used in the compositions of the present invention do not include any chelated metal species.

The Colour Index International is a standard classification system for dyes and pigments which contains historic, proprietary, generic names and generic numbers that have been applied to colours. It was first published in 1924 and has been updated and reprinted since. The $2^{nd}$ (1956), $3^{rd}$ (1971) and $4^{th}$ (2002) editions are jointly published and maintained by the Society of Dyers and Colourists (SDC) (UK) and American Association of Textile Chemists and Colourists (AATCC). The structures of the dye compounds shown in this specification are taken from the Colour Index International.

Examples of suitable dyes for use in component (i) of the composition of the first aspect include those of the following group, (1):

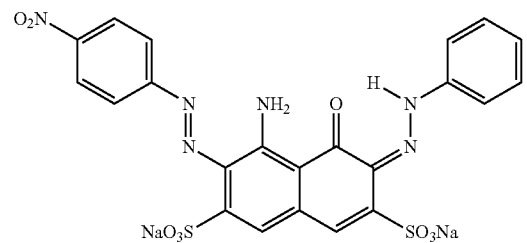

Compound (A) is known as Acid Black 1, Duramine Black 10B and Black-Blue 10B.

Compound (B) is known as Acid Orange 7 and Duramine Orange II.

Compound (C) is known as Acid Red 33 and D&C Red 33.

Compound (D) is known as Acid Yellow 23, Acid Tartrazine and Eurogran tartrazine.

Examples of suitable dyes include those of the following group, (2):

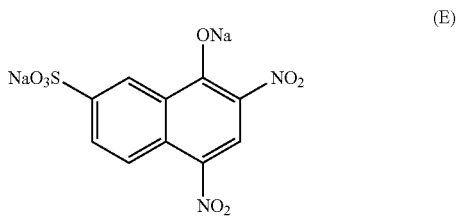

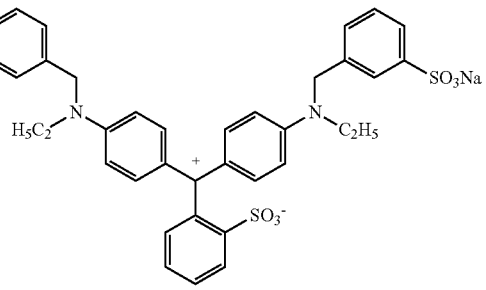

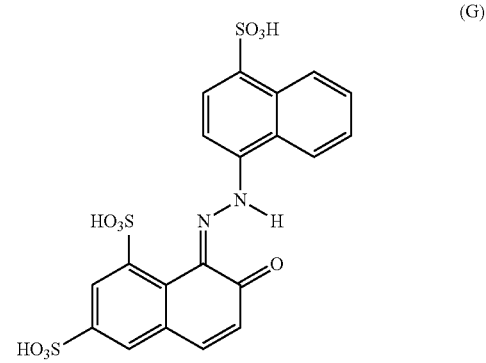

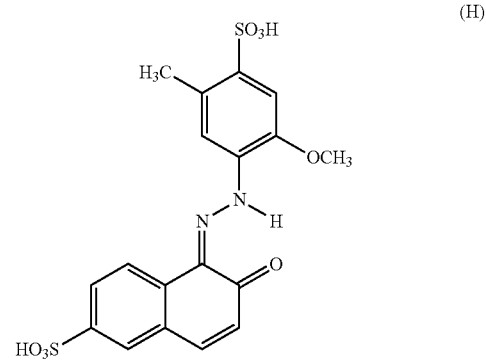

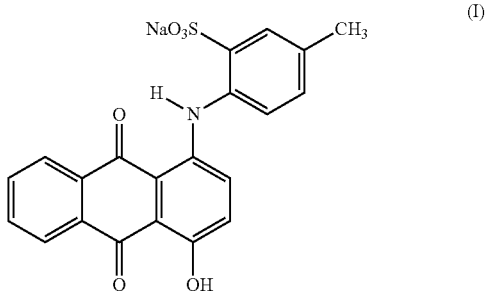

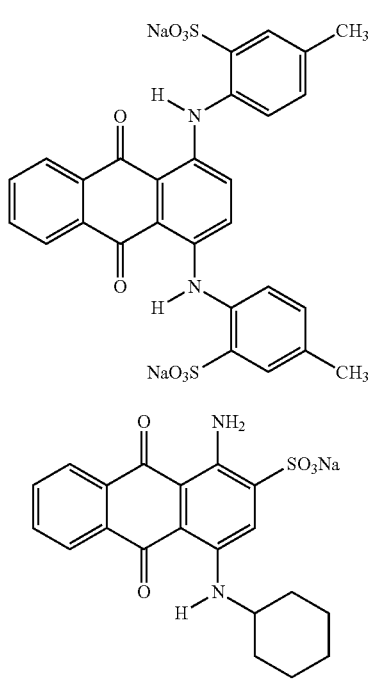
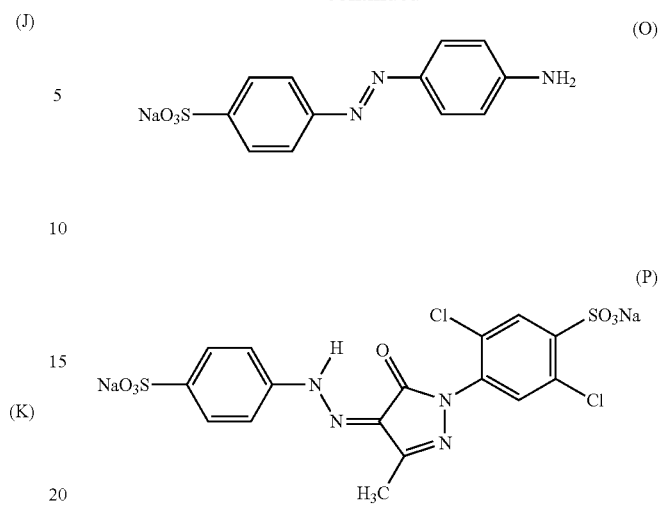

Compound (E) is known as Acid Yellow 1, Ext D&C Yellow 1 and Naphthol Yellow S.

Compound (F) is known as Acid Blue 9, Duracol Brilliant Blue FCF E133, Food Blue 2 and FD&C Blue 1.

Compound (G) is known as Acid Red 18, Duracol Ponceau 4R E124, Eurocert Ponceau 4R and Food Red 18.

Compound (H) is known as Food Red 17 and FD&C Red 40.

Compound (I) is known as Acid Violet 43 and Ext. D&C Violet 2.

Compound (J) is known as Acid Green 25 and D&C Green 5.

Compound (K) is known as Acid Blue 62, Acid Brilliant Blue R and Duramine Blue R.

Compound (L) is known as Acid Red 14, Food Red 3 and Duracol Carmoisine.

Compound (M) is known as Food Green 3 and D&C Green 3.

Compound (N) is known as Acid Red 1 and Lissamine Red 2G.

Compound (O) is known as Direct Orange 39 and Solar Orange 2GL.

Compound (P) is known as Acid Yellow 17, Duramine Yellow 2G and Acrolan Yellow 2G.

Examples of suitable dyes include those of the following group, (3):

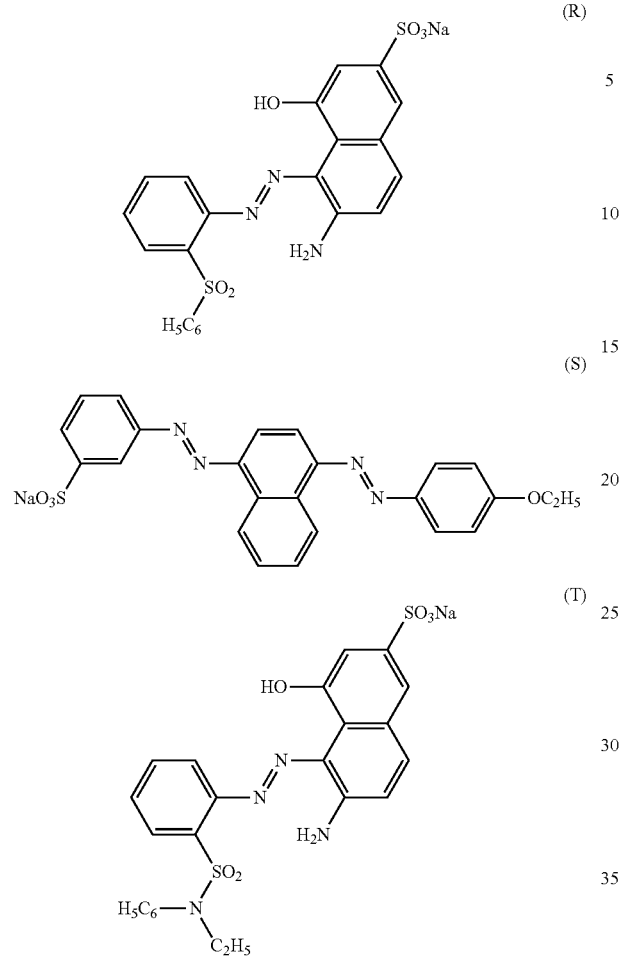

Compound (Q) is known as Acid Blue 113 and Telon Navy AMF.

Compound (R) is known as Acid Red 42, Telon Red BN and Acidol Red 2BE-NR.

Compound (S) is known as Acid Orange 127 and Nylosan Orange N-RL.

Compound (T) is known as Acid Red 57 and Duramine Red 3G.

Examples of suitable dyes include those of the following group, (4):

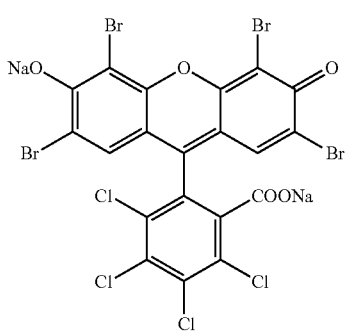

Compound (U) is known as Acid Red 92 and D&C Red 28.

Compound (V) is known as Acid Red 52, Acid Rhodamine B and Nylosan Rhodamine B.

Compound (W) is known as Tetrabromophenol Blue.

Compound (X) is known as Acid Yellow 3 and D&C Yellow 10.

The names given above represent a non-exhaustive list and compounds having the structures shown may also be known by other names. Although the above mentioned trade names may change, the skilled person would be able to consult the Colour Index International to identify the dye compound and find a current manufacturer.

Component (i) preferably comprises a dye compound selected from those in group (1), group (2), group (3) or group (4).

Preferably component (i) comprises a dye compound selected from those in group (1), group (2) or group (3).

More preferably component (i) comprises a dye compound selected from those in group (1) or group (2).

Most preferably component (i) comprises a dye compound selected from those in group (1).

The compositions of the present invention may include a mixture of two or more dye compounds. These may be selected from the same and/or different groups. They may be combined in a specific ratio to achieve a desired colour or other visual effect.

The colouring composition comprises at least 0.0001 wt % of the dye compound. Preferably it comprises at least 0.001 wt %, more preferably at least 0.01 wt %, suitably at least 0.05 wt %, preferably at least 0.1 wt %, for example at least 0.5 wt %. The colouring composition suitably comprises up to 40 wt % of the dye compound, preferably up to 30 wt %, more preferably up to 25 wt %, suitably up to 20 wt %, preferably up to 15 wt %, more preferably up to 12 wt %, for example up to 10 wt %.

The amount of dye included in the composition may vary significantly depending on the strength of colour it is desired to achieve.

The above amounts refer to the total amount of all dye compounds of component (i) present in the colouring composition (for application as a single composition). Commonly mixtures of two or more dyes will be included, the relative amount being dependent on the desired shade required and the preparation of such mixtures will be readily understood by those skilled in the art.

The colouring compositions of the present invention comprise at least 0.1 wt % urea. Without being bound by theory it is believed that urea helps to solubilise the dye compounds in the composition and/or denatures keratinous proteins found in hair (and animal fibres) and increases the rate of reaction with the fibre substrate. In addition urea helps to swell the hair.

Urea may suitably be present in the composition in an amount of at least 0.5 wt %, preferably at least 1 wt %, suitably at least 2 wt %, preferably at least 3% wt, for example at least 4 wt %.

Urea may suitably be present in an amount up to 40 wt % of the composition, preferably up to 30 wt %, more preferably up to 25 wt %, suitably up to 20 wt %, preferably up to 15 wt %, for example up to 12 wt % or up to 10 wt %.

The composition of the present invention preferably comprises less than 0.1 wt % thiourea.

Preferably the compositions of the present invention do not comprise thiourea.

The composition of the present invention comprises 0.1 to 2.5 wt % thiol.

Preferably the composition of the present invention comprises at least 0.25 wt % thiol, preferably at least 0.4 wt %, more preferably at least 0.5 wt %, preferably at least 0.6 wt %, suitably at least 0.7 wt %, for example at least 0.8 wt % or at least 0.9 wt %.

The composition may comprise up to 2.5 wt % thiol, preferably up to 2.2 wt %, more preferably up to 2 wt %, suitably up to 1.7 wt %, preferably up to 1.5 wt %, more preferably up to 1.3 wt %, for example up to 1.2 wt % or up to 1.1 wt %.

The composition of the present invention may comprise a mixture of thiols. In such embodiments the above amounts refer to all thiols present. Suitable thiols include thioglycolic acid, thiolactic acid, dihydrolipoate, thioglycerol, mercaptopropionic acid, cysteine, N-substituted cysteines, cysteamines, N-substituted cysteamines, thioethanol, thiosulfate, sulfide anion, 1-thiopropane 3-sulfonate, and salts and/or esters thereof.

An especially preferred thiol is thioglycolic acid. Thioglycolic acid may be provided as the free acid or as an ester or a salt.

Preferred salts include ammonium, substituted ammonium, alkali metal and alkaline earth metal salts.

Suitable esters include $C_1$ to $C_4$ esters and glycerol esters. The glycerol ester (glycerol trithioglycolate) may be used.

In some preferred embodiments thioglycolic acid may be added to the composition as the free acid but may be present as a salt due to the pH of the composition.

Preferably thioglycolic acid or a salt thereof is the only thiol present in the composition.

Preferably the composition comprises from 0.1 to 2.5 wt % thioglycolic acid, preferably from 0.5 to 1.5 wt %.

The composition comprises less than 0.5 wt % ammonia.

Most preferably the composition of the present invention is substantially free of ammonia. By this we mean that the composition is substantially free of ammonia and ammonia providing compounds, for example ammonium hydroxide.

The composition comprises less than 0.5 wt % sulfite ions. Preferably it comprises less than 0.4 wt %, preferably less than 0.3 wt %, more preferably less than 0.2 wt %, suitably less than 0.1 wt %, preferably less than 0.01 wt %, more preferably less than 0.001 wt %.

Most preferably the composition of the present invention is substantially free of sulfite ions. Sulfite ions are typically provided by sulfonic acid, or salts of sulfonic acid for example sodium sulfite.

By substantially free of ammonia and sulfite ions we mean that the compositions of the present invention do not contain any source of these compounds which have been added deliberately.

They may be present in trace amounts due to their presence as impurities in other components used in the composition.

The composition of the present invention suitably comprises less than 2 wt % fatty acids, preferably less than 1 wt %, more preferably less than 0.5 wt %. By this we mean that the composition preferably comprises less than 2 wt % of compounds of formula RCOOH wherein R is a $C_6$ to $C_{30}$ alkyl or alkenyl group.

The composition of the present invention suitably comprises less than 2 wt % enzymes, preferably less than 1 wt %, more preferably less than 0.5 wt %, preferably less than 0.1 wt %, more preferably less than 0.01 wt %, preferably less than 0.001 wt %, more preferably less than 0.0001 wt %, for example less than 0.00001 wt % enzymes. Preferably the composition of the present invention is substantially free from enzymes.

The colouring composition preferably comprises one or more solvents or diluents.

Suitable diluent materials for use in colouring compositions described herein may be selected from those specified on the INCI list (International Nomenclature of Cosmetic Ingredients list). This is drawn up by the Scientific Committee on Consumer Products (SCCP) managed by the Directorate-General for Health and Consumer Protection of the European Commission. The SCCP approve a list of chemicals for use in cosmetics which is referred to as the INCI list.

Water is the preferred diluent for use in the present colouring compositions. However, such compositions may include one or more further solvents as additional diluent materials. Generally, solvents suitable for use in the colouring compositions of the present invention are selected to be miscible with water and innocuous to the skin. Solvents suitable for use as additional diluents herein include $C_1$-$C_{20}$ mono- or polyhydric alcohols and their ethers, for example glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. Water is the preferred principal diluent in the compositions according to the present invention. Principal diluent, as defined herein, means that the level of water present is higher than the total level of any other diluents.

The composition of the present invention is preferably an aqueous composition. Preferably it comprises at least 20 wt % water, preferably at least 40 wt %, more preferably at least 60 wt %, suitably at least 70 wt %, for example at least 75 wt % or at least 80 wt %.

One especially preferred solvent is glycerol. This is suitably present in an amount of from 0.1 to 10 wt %, preferably 0.25 to 5 wt %, for example from 1 to 3 wt %.

Preferred dye compounds for use in the present invention are water soluble and completely dissolve to provide a substantially homogeneous aqueous colouring composition. However embodiments including dye compounds that are not completely water soluble or are water insoluble are also within the scope of the invention. In such embodiments the dye compound may suitably be present in the composition in the form of a suspension. Alternatively the dye compound may be first dissolved in a cosolvent. This may for example be a water miscible cosolvent.

The colouring compositions of the present invention may further comprise one or more surfactants. Suitable surfactants for use in compositions of the present invention may be found on the INCI list. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

Suitable surfactant compounds for use in the present invention are of the conventional type known for use in hair dye formulations and will be well understood by those skilled in the art. Preferred surfactants are those favoured by the cosmetic industry. These are typically gentle and non-allergenic and include, for example cocamidopropyl betaine and laurylamidopropyl betaine and sodium laureth sulfate.

The colouring composition of the present invention may typically comprise from 0.1 to 10 wt % of one or more surfactants, preferably from 0.5 to 2.5 wt %.

In addition to the surfactant compounds detailed above, additional amounts of compounds of this type may be present as a conditioning agent.

The hair colouring compositions of the present invention may additionally include a thickener, suitably a cosmetically approved thickener. This is preferably present in an amount of from 0.1 to 20 wt %, preferably from 0.5 to 5 wt %. Thickening agents suitable for use in the compositions herein include those specified on the INCI list. Preferred thickening agents suitable for use in the compositions of the present invention include oleic acid, cetyl alcohol, oleyl alcohol, sodium chloride, cetearyl alcohol, stearyl alcohol, synthetic thickeners such as Carbopol and Glucamate™ (The Lubrizol Corp, USA), Aculyn polymers (Rohm and Haas, USA) and mixtures thereof. An especially preferred thickener for use herein is hydroxyethyl cellulose.

The colouring compositions of the present invention preferably have a pH in the range of from 5 to 13, preferably from 8 to 11.5, more preferably from 9 to 10.5. In order to maintain such a pH the compositions may contain one or more optional pH control agents.

Preferred pH control agents for use herein include those specified on the INCI list, for example 2-amino-2-methyl-1-propanol and sodium hydroxide.

The colouring compositions of the present invention may be provided in any suitable form. For example they may be provided as a solution, paste, cream, lotion, gel, mousse foam, spray or the like. The composition is suitably of a viscosity which enables it to spread across the head easily during the hair dyeing process, and then stay in position on the head when required.

Preferably the material treated in the method of the second aspect is a keratinous material. More preferably it is a keratinous fibre material, although the method of the present invention may also be used to dye non-fibrous keratinous based material, for example finger or toe nails. Most preferably the method of the present invention is a method of dyeing hair, in particular human hair.

In preferred embodiments of the method of the second aspect of the present invention the composition is preferably applied to the material (suitably hair), and maintained in contact with the material at a temperature of at least 0° C., preferably at least 10° C., for example at least 20° C. It may suitably be applied and maintained at a temperature of up to 70° C., for example up to 60° C. or up to 50° C. A temperature of approximately 40° C. is particularly preferred. As will be appreciated by the person skilled in the art, when the material being dyed is human hair a suitable hood may be used to achieve the desired temperature.

It has been found that improved dyeing can be achieved if the composition is contacted with the hair at a temperature above ambient temperature.

Thus in preferred embodiments the method of the second aspect of the present invention comprises contacting the material with a colouring composition of the first aspect at a temperature of at least 30° C., suitably at a temperature of between 30° C. and 50° C., preferably between 35° C. and 45° C.

The composition is preferably contacted with the material for a period of at least 1 minute, preferably at least 2 minutes, more preferably at least 5 minutes, for example at least 10 minutes, or at least 15 minutes.

It may be contacted with the material for a period of up to 4 hours, suitably up to 3 hours, preferably up to 2 hours, for example up to 1.5 hours. A contact time of 30 to 60 minutes is especially preferred.

The colouring composition may be applied to the hair by any suitable means. Such methods are well known to those skilled in the art and include for example brushing the composition (which may suitably be in the form of a paste) onto the hair.

The compositions may be suitably applied to hair at a liquor ratio of from 10:1 to 0.5:1, preferably from 5:1 to 1:1, for example from 3:1 to 2:1.

The compositions may suitably be rinsed from the hair with warm water.

In some preferred embodiments in the method of the present invention the hair is subsequently treated with an oxidising composition.

In preferred embodiments the method of the second aspect involves the steps of:
 (a) contacting the material with a composition of the first aspect;
 (b) rinsing the material; and
 (c) contacting the material with an oxidising composition.

As mentioned above the material is preferably hair, especially human hair.

The oxidising composition contacted with the hair in step (c) preferably comprises a source of peroxide. Preferably it comprises hydrogen peroxide. The oxidising composition preferably comprises from 0.1 to 10 wt %, preferably 0.25 to 2.5 wt %, for example 0.5 to 1.5 wt % hydrogen peroxide.

The oxidising composition is preferably an aqueous composition. It is preferably a shampoo composition. By this we mean that in addition to a source of peroxide, the composition suitably comprises components typically found in a commercial shampoo formulation. Thus the oxidising composition may comprise a mixture of surfactants, suitably including anionic, cationic and non-ionic surfactants; along with other ingredients for example thickeners, solvents, colourants, fragrances, preservatives, antioxidants, chelating agents, emollients and biocides.

The oxidising composition is preferably acidic. It may comprise any suitable acid. Preferred acids include acetic acid and citric acid. Preferably the oxidising composition has a pH of from 3 to 6, preferably from 3.5 to 4.5.

Preferably the oxidising composition is applied to the hair using the same liquor ratio as described above. Suitably it is allowed to remain on the hair for a period of 1 to 20, preferably 2 to 10 minutes.

In some embodiments, the method of the present invention may include a further step in which the hair is treated with a composition to impart a particular property, for example improved wash fastness or soft handle. Such a composition may be provided in any suitable form for example a solution, cream, foam, mousse, spray or gel. One suitable after-treatment comprises applying a composition comprising a hair conditioning agent. Such conditioning compositions are well known to those skilled in the art and any commercially available conditioning composition could be used.

In some preferred embodiments the method of the second aspect of the present invention involves a further step (d) of contacting the material, preferably hair, with a conditioning composition comprising a quaternary ammonium compound.

Preferably the material (suitably hair) is rinsed between steps (c) and (d), suitably with warm water. The conditioning composition contacted with the hair in step (d) preferably comprises at least 0.1 wt % of one or more quaternary ammonium compounds, preferably at least 0.5 wt %, more preferably at least 1 wt %, suitably at least 2 wt % or at least 3 wt %.

The conditioning composition may comprise up to 20 wt % of one or more quaternary ammonium compounds, preferably up to 15 wt %, suitably up to 12 wt %, preferably up to 10 wt %, for example up to 6 wt %.

Mixtures of quaternary ammonium compounds may be present. The above amounts refer to the total of all such compounds in the conditioning composition.

Suitable quaternary ammonium compounds include those compounds containing a single quaternary ammonium cationic centre and compounds including multiple quaternary ammonium cationic centres, for example polymeric compounds.

Suitable quaternary ammonium compounds include alkyl trimethylammonium halides wherein the alkyl group has from 14 to 24 carbon atoms.

Preferred quaternary ammonium compounds include cetyltrimethyl ammonium chloride, stearyltrimethyl ammonium chloride, behenyltrimethyl ammonium chloride and mixtures thereof.

Suitable quaternary ammonium compounds include polycationic polymers containing multiple quaternary ammonium centres referred to on the INCI list as "Polyquaternium" compounds. The composition of the present invention may include any polyquaternium compound listed on the INCI list. Other suitable compounds include polycationic polyamine compounds used in the textile/paper industry for improving wash fastness of dyes or dyeability. Examples of such compounds include, but are not limited to, polymers made by condensing dicyandiimide and diethylene triamine.

The conditioning composition is preferably acidic. It suitably has a pH of between 2 and 5, preferably between 3 and 4.

The method of the second aspect of the present invention is preferably a method of dyeing hair. Suitably the method is not a method of waving hair. Preferably the method of the present invention does not cause permanent waving of the hair.

In some embodiments the composition of the first aspect of the present invention may be first prepared from two precursor compositions.

According to a third aspect of the present invention there is provided a method of preparing a colouring composition of the first aspect, the method comprising admixing a first precursor composition comprising component (i) and a second precursor composition comprising component (iii).

The amount of each component present in each of the first and second precursor compositions is suitably selected such that admixture of the two precursor compositions in an appropriate ratio provides the compositions of the first aspect. Examples of suitable precursor compositions are given in the examples described herein. However these are intended to be in no way limiting and alternative precursor compositions which may be mixed to provide compositions of the second aspect for use in the method of the first aspect are also within the scope of the present invention. The person skilled in the art would readily understand how to prepare such compositions. Either or each of the first and second precursor compositions may comprise one or more of the additional ingredients as mentioned herein. Component (ii), urea is preferably provided in the second precursor composition but may alternatively or additionally be included in the first precursor composition.

In a fourth aspect the present invention provides a packaged hair colouring product. This may comprise a composition of the first aspect along with suitable packaging. Preferably the packaged hair colouring product comprises a first package comprising a first precursor composition comprising component (i) and a second package comprising a second precursor composition comprising component (iii).

The first package and second package may be of any suitable form. Suitably the first and second precursor compositions may be mixed to form a composition of the first aspect.

In one embodiment the packaged hair colouring product may be provided in a bicompartment container in which the first precursor composition is held in a first compartment and the second precursor composition is held in a second compartment, of the same container. Preferably the bicompartment container is arranged to deliver the first and second precursor compositions to the same locus. This may be achieved by providing adjacent outlets from the first and second compartments. Alternatively, the first and second compartments may deliver the first and second precursor compositions into a common passageway in which they are contacted prior to exiting the container through a single outlet. Bicompartment containers of this type are known to the person skilled in the art. One such example is a squeezable tube (known as a "dual tube") having two compartments comprising the two precursor compositions. Squeezing the tube causes the two compositions to be delivered through adjacent outlets such that they come into immediate contact with each other on exiting the container. Other embodiments of bicompartment containers also include bottles or canisters for holding mousses, gels or sprays which are provided with a single actuator which effects delivery of the two precursor compositions to the same locus via the same or adjacent outlets.

Alternatively the hair colouring product of the present invention may be provided as two discrete precursor compositions which are packaged separately in individual containers. In such embodiments, the packaged hair colouring product may further comprise instructions for preparing the active colouring composition of the second aspect.

In some embodiments the packaged hair colouring product may further comprise a utensil for application of the colouring composition to the hair, for example a brush or a spatula. In some embodiments the packaged product may further comprise equipment for preparing the colouring composition from the precursor compositions, for example a mixing container and/or stirrer.

In some embodiments in which the packaged hair product comprises separate first and second packages comprising first and second precursor compositions which are combined prior to application to the hair, each of the precursor compositions may be provided in any suitable form. Each may be a solid, a liquid, a paste or gel.

In some embodiments each of the first and second precursor compositions may be a solid to which a solvent, suitably water must be added to form the colouring composition of the first aspect.

In some embodiments one of the first or second precursor compositions is a liquid composition and the other is a solid composition. Admixture of the first and second precursor compositions may in such embodiments directly form a composition of the second aspect.

Where one or both of the first and second compositions is a paste, gel or cream a composition of the second aspect may be directly obtained on admixture.

In some embodiments the first and second precursor compositions may each contain part of a bi-component thickener such that mixing the compositions leads to an increase in viscosity. In such a manner two liquid compositions for example could be combined to form a paste or cream having a consistency to enable it to be easily applied to the hair without running off. Suitable bi-component thickeners are known to the person skilled in the art. It would also be possible to include thickeners which change viscosity upon a change in pH.

The packaged hair colouring product of the present invention preferably comprises instructions for colouring hair.

In some embodiments in which the product comprises first and second packages comprising first and second precursor compositions, the packaged hair colouring product may further comprise instructions for preparing the active hair colouring composition.

It has been surprisingly found that hair coloured by the method of the present invention has superior wash fastness compared to hair coloured by methods of the prior art. For example, a so-called "permanent" colouring composition of the prior art of the type formed in situ from dye precursor compounds would show some colour fading following five shampooing applications. However hair coloured by the method of the present invention suitably shows substantially no fading after ten washes, preferably after fifteen washes, more preferably after twenty washes. Thus the method of the second aspect of the present invention may be regarded as a method of permanently dyeing hair.

Without wishing to be bound by theory it is believed that the dye compounds used in the present invention may form a variety of types of interactions with the hair fibres for example electrostatic interactions, hydrophobic interactions and aromatic interactions. The interactions may be dye-dye interactions or dye-keratin interactions.

Without wishing to be bound by any theory it is believed that the thiol applied to the hair in the method of the present invention may react with some disulfide bonds in the keratin fibres cleaving them and allowing them to swell. This may facilitate dye diffusion leading to increased interactions and thus lead to improved wash fastness.

It is also believed that the anionic carboxylate and/or sulfonate groups present in the dye compounds used in the compositions of the present invention interact with the guanidinium cations present in arginine residues of the hair. These guanidinium cations have a $pk_a$ of 12.5 and thus may be regarded as permanent cations at pH values below this.

The method of the present invention has been found to be particularly effective when used to colour hair that has first been peroxide bleached. Again without wishing to be bound by theory it is believed that pre-bleaching may help open up the structure of the hair and thus allow better penetration of the dye within the hair.

Thus the method of the present invention may include a first step of peroxide bleaching the hair prior to colouring to provide a lighter initial colour and a different overall result.

This first bleaching step may be carried out by use of percarbamic acid and/or a diacyl percarbamate, generated in situ by the method of the applicant's earlier patent EP 1313830B.

Preferably however the bleaching is carried out using the improved mild bleaching method described in the applicant's co-pending applications GB0816943.5, GB0907800.7 and PCT/GB2009/051157.

This mild bleaching method preferably comprises applying to the hair a composition comprising at least 10 wt % of ammonium carbonate, ammonium carbamate or a mixture thereof and a source of hydrogen peroxide. Preferred features of the bleaching step are as defined in the above-mentioned applications.

Although the above mentioned bleaching methods are preferred, other bleaching methods could also be used. Such methods are known to the person skilled in the art.

If it is desired to remove colour from the hair following the colouring method of the present invention, this could be achieved by applying to the hair a composition comprising a chemical agent able to reduce the chromophore moiety. Such compositions are well known to those skilled in the art and the removal of the colour in such circumstances is readily achieved.

However in preferred embodiments colour removal is effected using a colour removal method such as is described in the applicant's co-pending applications GB0816943.5 and PCT/GB2009/050233 and PCT/GB2009/051162.

As described in these applications the present inventors have developed a particularly effective composition and method which can be used to remove colour from dyed hair. The inventors have found that this colour removal method is particularly effective at removing colour from hair treated according to the method of the present invention. Thus, the present invention may further include a hair colour removal method.

The colour removal method is not a bleaching method. Indeed the colour removal method is particularly advantageous because it does not involve oxidative bleaching of the hair and thus avoids the damage that colour removal by bleaching may cause.

The hair colour removal method of the present invention preferably comprises applying to dyed hair, preferably hair dyed by the method of the second aspect, a colour removal composition comprising a nucleophile, or a precursor thereof. Preferably the colour removal composition comprises a sulfur-containing nucleophile, or a precursor thereof. Suitable sulfur-containing nucleophiles include thiocyanate, thioglycolic acid, thiocarbamate, carbamoylsulphinic acid and mixtures and/or salts thereof. Alternatively and/or additionally, the colour removal composition may comprise a nucleophile precursor. One suitable nucleophile precursor is thiourea dioxide. Thiourea dioxide is not nucleophilic in itself but rearranges to form formamidine sulfinic acid which hydrolyses to form the nucleophilic species $HSO_2^-$ (hydrosulfoxylate).

In especially preferred embodiments the sulfur-containing nucleophile comprises a salt of sulphoxylic acid of formula $HSO_2^{-+}M$. M is preferably hydrogen, an alkali metal or a quaternary ammonium species. Such salts may suitably be generated from formamidine sulphinic acid, dithionite ($S_2O_4^{2-}$).

Under acidic conditions formamidine sulphinic acid exists as the thiourea dioxide tautomer but under mildly alkaline conditions the formamidine tautomer is formed which hydrolyses to release $HSO_2^{-+}M$ which is believed to be the active dye removal agent. It is also possible to use mixed formamidine/carbamoyl sulphinic acids to generate the reactive species.

The colour removal composition comprises preferably at least 0.1 wt % of the sulfur-containing nucleophile or precursor thereof, more preferably at least 1 wt %, most preferably at least 4 wt %.

Suitably the colour removal composition comprises up to 60 wt % of the sulfur-containing nucleophile or precursor thereof, preferably up to 45 wt %, more preferably up to 30 wt % and most preferably up to 15 wt %.

The colour removal composition may comprise a mixture of sulfur-containing nucleophiles or precursors thereof. In such embodiments the above amounts refer to all such nucleophiles or precursors thereof present in the composition.

In some preferred embodiments the colour removal composition comprises from 0.1 to 10 wt %, preferably 3 to 7 wt % thiourea dioxide and from 0.1 to 2.5 wt %, preferably 0.5 to 1.5 wt % thioglycolic acid.

The colour removal composition may further comprise one or more of a swelling agent, an activator, a diluent, a conditioning agent, a pH buffer, a thickener and one or more surfactants.

Other optional excipients may also be present. Preferred ingredients for use as a conditioning agent and the like include those detailed on the INCI list.

Suitable swelling agents include urea. This may be present in an amount of from 1 to 50 wt %, preferably 15 to 25 wt %.

Suitable activators include divalent and trivalent metal species, for example divalent and/or trivalent ions of zinc, magnesium, aluminium and calcium. Zinc acetate and magnesium acetate are particularly preferred.

The activator is suitably present in the colour removal composition in an amount of from 0.5 to 25 wt %, preferably 2.5 to 15 wt %.

The preferred diluent is water. This is suitably present in an amount of from 10 to 90 wt %.

Suitable pH buffers include 2-amino-2-methyl-1-propanol.

Suitably the colour removal composition has a pH of from 6 to 12, more preferably from 7.5 to 10.5, and most preferably from 8.5 to 9.5.

A preferred thickener is hydroxyethylcellulose. Preferably the colour removal composition comprises from 1 to 20 wt % of thickeners.

The composition may comprise from 0.1 to 20 wt % of one or more surfactants. Suitable surfactants include anionic, cationic, nonionic and amphoteric surfactants. Preferred are nonionic surfactants, especially alkoxylated nonionic surfactants. One suitable nonionic surfactant is polysorbate 80.

In order to maximise the shelf life of the colour removal composition, it can be packaged as a two or three component system which could be mixed together shortly before use. By utilising a two or three pack system, it is possible to make compositions that when combined produce a thickened product which is more suitable for use on hair.

The colour removal composition is suitably applied to the hair and maintained on the head at a temperature of from 10 to 75° C., preferably from 20 to 70° C., more preferably from 30 to 65° C.

When removing colour from human hair at temperatures above ambient temperature a suitable hood can be employed to achieve the required temperature.

Suitably complete colour removal is effected after a period of 5 to 120, for example 15 to 90 minutes. Suitably the colour removal composition is left in the hair for a period of from 0.1 to 300 minutes, preferably 15 to 90 minutes for example 30 to 60 minutes.

Colour removal from hair dyed by the method of the present invention has been found to be very effective. Hair has been found to return to its original colour prior to being dyed without any visible damage occurring. In embodiments in which an initial bleaching step has been carried out, hair has been found to return to its bleached colour.

This method offers considerable advantages over colour removal methods of the prior art which rely on bleaching the hair. Such bleaching colour removal methods of the prior art cause considerable damage to hair (particularly in the case of hair which is repeatedly dyed and oxidatively bleached) and often do not provide the original colour.

It is also known from the prior art to use aminomethanesulfinic acid for colour removal. Under the conditions used, this would not act as a nucleophile but for the avoidance of doubt, the nucleophilic colour removal species of the present invention does not comprise aminomethanesulfinic acid. In any case aminomethanesulfinic acid may, like oxidative bleaching agents, cause damage to the hair and is not as effective as the colour removal systems of the present invention for removing colour applied by the method of the invention.

The present invention thus provides a hair treatment method comprising the steps of:
  (x) optionally bleaching hair by applying a bleaching composition comprising ammonium carbonate or a divalent metal cyanate and a source of hydrogen peroxide;
  (y) dyeing the hair by the method of the first aspect; and
  (z) optionally removing colour from the hair by applying a colour removal composition comprising nucleophilic colour removal species.

Preferred aspects of each of steps (x), (y) and (z) are described above. Steps (y) and (z) may be repeated without any significant damage occurring to hair. Preferably steps (y) and (z) may be each repeated two or more, preferably five or more, for example ten or more times without any significant increased damage to the hair being observed.

Step (x) is an optional mild initial bleaching step. This is carried out if it is desired to lighten the initial colour of hair prior to a first dyeing step. However, once a first colour has been applied, there is no need to again bleach the hair further to remove this colour as this can be carried out in step (z). Step (x) would be repeated only if a lighter base shade is required. Of course it will also be necessary to bleach new hair which has grown since previous colouring.

Because step (x) and in particular steps (y) and (z) can be carried out rapidly, it would be possible for a user to dye a small portion of hair (either on or off the head) to see exactly the colour that would be achieved and remove this colour if it was not desirable.

The colouring method of the present invention is highly reproducible, rapidly develops to full colour, is resistant to fade and readily removable, and thus offers considerable advantages over the prior art. In particular, when using colouring methods and compositions of the prior art, the final colour of the dyed hair is often unpredictable and relies on the skill of a hairdresser to achieve a close match to the desired colour. The colouring compositions of the present invention can be used in combination with a colour measurement apparatus to accurately measure a desired shade and produce a formula to achieve this colour on the hair. This type of colour match prediction is based on software currently used throughout the textile industry and the paint industry.

The method of the present invention may be used to dye some or all of the hair on the head of a human. Thus all of the hair may be dyed a single colour. Alternatively small sections of the hair may be coloured to provide "streaks" or "highlights/lowlights". In some embodiments new hair at the roots may be coloured to match an existing colour on the body of the hair. A different colour on sections of hair could also be achieved by selective application of the colour removal composition to dyed hair.

Although the present invention relates primarily to the dyeing of a material, for example human hair, in a single application (i.e. only one composition comprising a dye compound or compounds is applied), it could also be used to repeatedly dye and thus gradually build up colour on a material.

For example it may be desired to gradually colour human hair, for example to add colour to grey hair. Thus the method of the first aspect of the present invention may be repeated periodically. This may for example be daily, weekly or monthly. In order to allow a gradual build up of colour to be achieved it would be necessary to adjust the amounts of dye compound present in the compositions applied to the hair accordingly. Such adjustments could be readily made by the person skilled in the art.

In some such embodiments the composition of the second aspect may be provided as a shampooing composition. This may for example be in the form of a "colour enhancing" shampoo which gradually adds colour to the hair upon repeated application.

The invention will now be further described with reference to the following non-limiting examples.

EXAMPLE 1

A composition comprising the following formulation provided a Neutral 4 colour when applied to bleached light brown hair.

| Part 1 - Colour Tube | |
|---|---|
| Acid Black 1 | 1.5925% |
| Acid Orange 7 | 1.25% |
| Acid Red 33 | 0.265% |
| Glycerol | 4% |
| Sodium laureth sulphate | 2% |
| Hydroxyethylcellulose | 2% |
| Perfume | 0.05% |
| Water | 88.8425% | pH adjusted to 9.5 with sodium hydroxide

| Part 2 - Colour gel | |
|---|---|
| Water | 84.3% |
| Urea | 10% |
| Aminomethyl propanol* | 2.7% |
| Thioglycolic acid | 2% |
| Hydroxyethylcellulose | 1% |

*pH adjusted to 9.5 with aminomethyl propanol

The hair treatment mixture was prepared by mixing parts 1 and 2 in a 1:1 ratio. The required amount of this mixture was brushed onto the hair to provided an even coverage and left at 40° C. for 30-60 minutes (as required). The skilled person is able to judge when a sufficient period has elapsed. The hair was rinsed with warm water.

An after-treatment shampoo (containing 1% Hydrogen Peroxide @ pH4) was massaged into the hair and then rinsed away with water.

A conditioning composition (containing a cationic conditioning agent @ pH3.5) was massaged into the hair and then rinsed away with water.

The hair was dried as required.

EXAMPLE 2

Comparative

A composition comprising the following formulation provided a Neutral 4 colour when applied to bleached light brown hair.

| Part 1 - Colour Tube | |
|---|---|
| Acid Black 1 | 1.5925% |
| Acid Orange 7 | 1.25% |
| Acid Red 33 | 0.265% |
| Glycerol | 4% |
| Sodium laureth sulphate | 2% |
| Hydroxyethylcellulose | 2% |
| Perfume | 0.05% |
| Water | 88.8425% | pH adjusted to 9.5 with sodium hydroxide

| Part 2 - Colour gel | |
|---|---|
| Urea | 10% |
| Aminomethyl propanol* | 2.7% |
| Thioglycolic acid | 4% |
| Sodium sulfite | 4% |
| Hydroxyethylcellulose | 1% |
| Water | balance |

*pH adjusted to 9.5 with aminomethyl propanol

The hair treatment mixture was prepared by mixing parts 1 and 2 in a 1:1 ratio. The required amount of this mixture was brushed onto the hair to provided an even coverage and left at 40° C. for 60 minutes (as required). The hair was rinsed with warm water.

An after-treatment shampoo (containing 1% Hydrogen Peroxide @ pH4) was massaged into the hair and then rinsed away with water.

A conditioning composition (containing a cationic conditioning agent @ pH3.5) was massaged into the hair and then rinsed away with water.

The hair was dried.

EXAMPLE 3

Hair tresses treated according to example 1 and example 2 were each combed 20 times. Photographs of the tresses are shown in FIG. 1. As can be seen the hair tresss dyed using a composition according to the invention (example 1) showed no breakage of the hair, whereas the hair tress dyed using a composition falling outside the claim (example 2) showed significant breakage.

EXAMPLE 4

A composition comprising the following formulation provided a black colour when applied to bleached light brown hair.

| Part 1 - Colour Tube | |
| --- | --- |
| Acid Black 1 | 2% |
| Glycerol | 4% |
| Sodium laureth sulphate | 2% |
| Hydroxyethylcellulose | 2% |
| Perfume | 0.05% |
| Water | balance |
| pH adjusted to 9.5 with sodium hydroxide | |

| Part 2 - Colour gel | |
| --- | --- |
| Urea | 10% |
| Aminomethyl propanol* | 2.7% |
| Thioglycolic acid | 2% |
| Hydroxyethylcellulose | 1% |
| Water | balance |
| *pH adjusted to 9.5 with aminomethyl propanol | |

The hair treatment mixture was prepared by mixing parts 1 and 2 in a 1:1 ratio. The required amount of this mixture was brushed onto the hair to provided an even coverage and left at 40° C. for 30 minutes. The hair was rinsed with warm water.

An after-treatment shampoo (containing 1% Hydrogen Peroxide @ pH4) was massaged into the hair and then rinsed away with water.

A conditioning composition (containing a cationic conditioning agent @ pH3.5) was massaged into the hair and then rinsed away with water.

The hair was dried.

EXAMPLE 5

Comparative

A composition comprising the following formulation provided a black colour when applied to bleached light brown hair.

| Part 1 - Colour Tube | |
| --- | --- |
| Acid Black 1 | 2% |
| Glycerol | 4% |
| Sodium laureth sulphate | 2% |
| Hydroxyethylcellulose | 2% |
| Perfume | 0.05% |
| Water | balance |
| pH adjusted to 9.5 with sodium hydroxide | |

| Part 2 - Colour gel | |
| --- | --- |
| Urea | 10% |
| Aminomethyl propanol* | 2.7% |
| Thioglycolic acid | 6% |
| Hydroxyethylcellulose | 1% |
| Water | balance |
| *pH adjusted to 9.5 with aminomethyl propanol | |

The hair treatment mixture was prepared by mixing parts 1 and 2 in a 1:1 ratio. The required amount of this mixture was brushed onto the hair to provided an even coverage and left at 40° C. for 30 minutes (as required). The hair was rinsed with warm water.

An after-treatment shampoo (containing 1% Hydrogen Peroxide @ pH4) was massaged into the hair and then rinsed away with water.

A conditioning composition (containing a cationic conditioning agent @ pH3.5) was massaged into the hair and then rinsed away with water.

The hair was dried.

EXAMPLE 6

Figure 2:
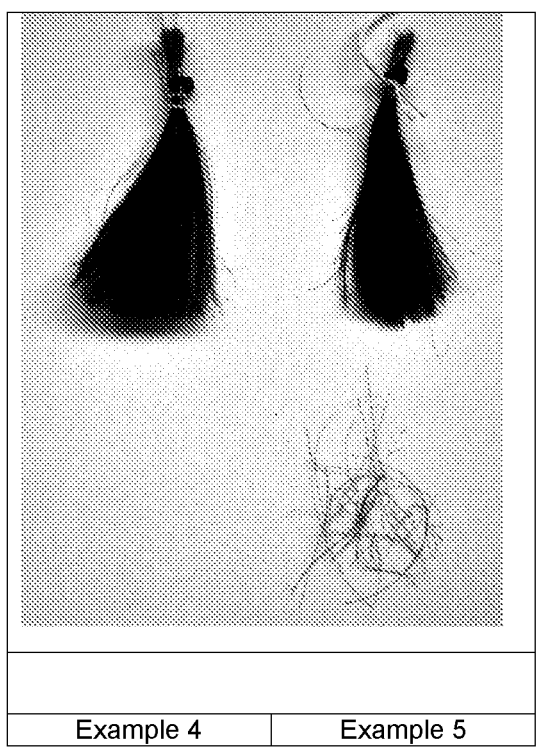
FIG. 2 is a photograph showing hair tresses treated according to Example 4 (left side of the photograph) and Example 5 (right side of the photograph).). Hair tresses treated with the composition of Example 4 showed no breakage of the hair while hair treated with the composition of Example 5 showed significant breakage.

Hair tresses treated according to example 4 and example 5 were each combed 20 times. Photographs of the tresses are shown in FIG. 2. As can be seen the hair tresss dyed using a composition according to the invention (example 4) showed no breakage of the hair, whereas the hair tress dyed using a composition falling outside the claim (example 5) showed significant breakage.

EXAMPLE 7

Comparative

A composition comprising the following formulation provided a Neutral 4 colour when applied to bleached light brown hair.

| Part 1 - Colour Tube | |
| --- | --- |
| Acid Black 1 | 1.5925% |
| Acid Orange 7 | 1.25% |
| Acid Red 33 | 0.265% |
| Glycerol | 4% |
| Sodium laureth sulphate | 2% |
| Hydroxyethylcellulose | 2% |
| Perfume | 0.05% |
| Water | 88.8425% |
| pH adjusted to 9.5 with sodium hydroxide | |

| Part 2 - Colour gel | |
| --- | --- |
| Urea | 10% |
| Aminomethyl propanol* | 2.7% |
| Hydroxyethylcellulose | 1% |
| Water | balance |
| *pH adjusted to 9.5 with aminomethyl propanol | |

The hair treatment mixture was prepared by mixing parts 1 and 2 in a 1:1 ratio. The required amount of this mixture was brushed onto the hair to provided an even coverage and left at 40° C. for 60 minutes (as required). The hair was rinsed with warm water.

An after-treatment shampoo (containing 1% Hydrogen Peroxide @ pH4) was massaged into the hair and then rinsed away with water.

A conditioning composition (containing a cationic conditioning agent @ pH3.5) was massaged into the hair and then rinsed away with water.

The hair was dried.

Figure 3:
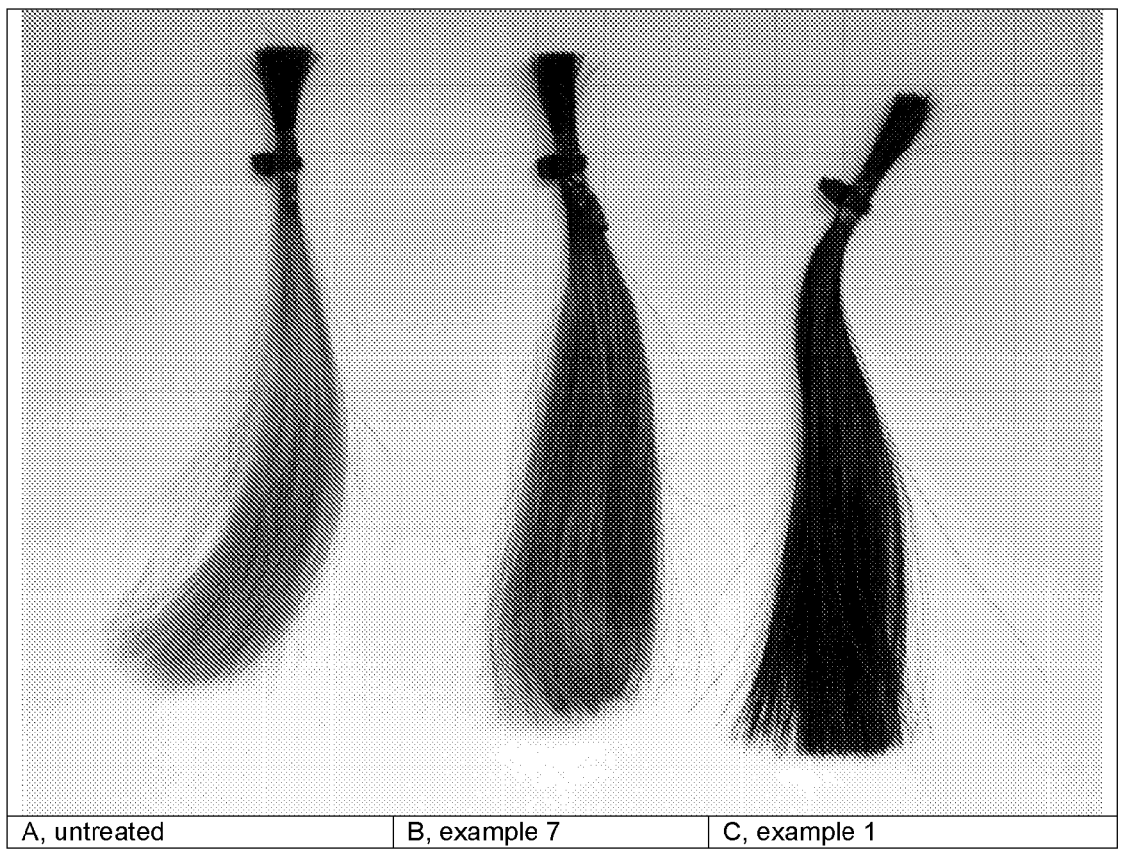
FIG. 3 is a photograph showing three hair tresses.

FIG. 3 shows pictures of three hair tresses. Tress A has is un-dyed bleached dark brown hair; tress B is hair dyed using the above formulation (example 7, comparative); tress C shows hair dyed according to the invention (example 1). This figure shows that improved colouration was achieved when using the composition of the invention.

EXAMPLE 8

Figure 4:
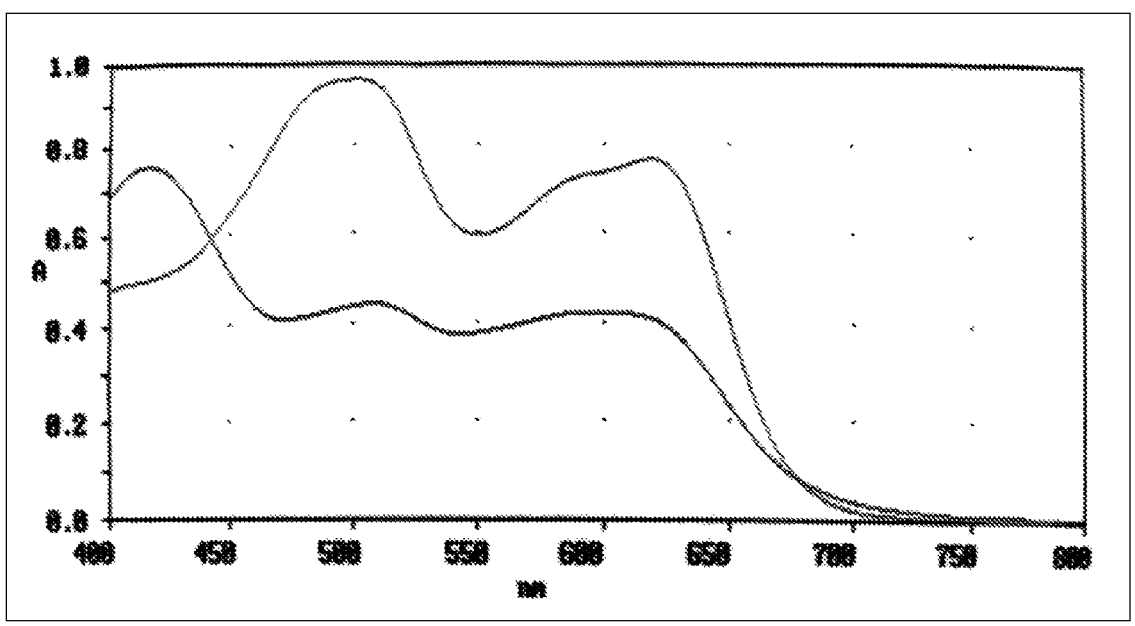
FIG. 4 is a graph showing the results of the analysis of dye residues following treatment with the compositions of Example 1 and 2 using a UV-visible spectrometer. The upper spectrum is for the dye residue following treatment according to Example 1 (brown) and the lower spectrum is for the dye residue following treatment according to Example 2 (green).

Dye residues following treatment with the compositions of example 1 and example 2 were analysed using a UV-visible spectrometer. The results are shown in FIG. 4. The upper spectrum is for the dye residue following treatment according to example 1 and is brown in colour. The lower spectrum is for the dye residue following treatment according to example 2 and is green in colour. Thus the composition of example 2 leads to a change in colour of the dye which is obviously highly undesirable.

The invention claimed is:

1. A colouring composition comprising:
   (i) at least 0.0001 wt % of a water-soluble dye compound containing one or more sulfonate and/or carboxylate groups;
   (ii) at least 0.1 wt % urea;
   (iii) from 0.1 to 2.5 wt % of a thiol;
   (iv) less than 0.5 wt % ammonia; and
   (v) less than 0.5 wt % sulfite ions
   wherein the composition comprises less than 2 wt % fatty acids and at least 75 wt % water.

2. A colouring composition according to claim 1 comprising from 2 to 15 wt % urea.

3. A colouring composition according to claim 1 wherein the thiol is selected from thioglycolic acid, thiolactic acid, dihydrolipoate, thioglycerol, mercaptopropionic acid, cysteine, N-substituted cysteines, cysteamines, N-substituted cysteamines, thioethanol, thiosulfate, sulfide anion, 1-thiopropane 3-sulfonate, and salts and/or esters thereof.

4. A colouring composition according to claim 3 wherein the thiol is thioglycolic acid or a salt thereof.

5. A colouring composition according to claim 1 which has a pH from 8 to 11.5.

6. A method of colouring a material, the method comprising contacting the material with a colouring composition as claimed in claim 1.

7. A method of coloring a material which involves the steps of:
   (a) contacting the material with a composition as claimed in claim 1;
   (b) rinsing the material; and
   (c) contacting the material with an oxidising composition.

8. A method according to claim 7 wherein the oxidising composition is acidic.

9. A method according to claim 7 which further involves a step (d) of contacting the material with a conditioning composition comprising a quaternary ammonium compound.

* * * * *